United States Patent [19]

Hill et al.

[11] Patent Number: 5,057,308

[45] Date of Patent: Oct. 15, 1991

[54] METHOD OF TREATING THE ORAL CAVITY WITH ORAL HYGIENE PREPARATIONS CONTAINING ACTIVE $SNF_2$

[76] Inventors: Ira D. Hill, Clay Ct., Locust, N.J. 07760; Robert D. White, 65 Glen Grey Rd., Oakland, N.J. 07436

[21] Appl. No.: 535,913

[22] Filed: Jun. 8, 1990

Related U.S. Application Data

[63] Continuation-in-part of Ser. No. 927,752, Nov. 6, 1986, and Ser. No. 927,805, Nov. 6, 1986, Pat. No. 4,950,479.

[51] Int. Cl.$^5$ .......................... A61K 7/18; A61K 7/16
[52] U.S. Cl. .......................... 424/52; 424/49; 424/56; 239/350; 222/402.1; 222/402.12; 222/424.5; 514/900; 514/901; 514/902; 514/835; 514/944
[58] Field of Search ............ 424/49, 52, 56, 439; 514/901, 835, 902, 900, 944; 239/350; 222/402.1, 402.12, 424.5

[56] References Cited

U.S. PATENT DOCUMENTS

| | | | |
|---|---|---|---|
| 185,666 | 12/1876 | Brown | 424/49 |
| 428,033 | 5/1890 | Alson | 424/49 |
| 872,908 | 12/1907 | Cutter | 424/49 |
| 1,069,874 | 8/1913 | Hanscom | 424/49 |
| 1,105,739 | 8/1914 | Wunsche | 424/49 |
| 1,149,376 | 8/1915 | Leonard et al. | 424/49 |
| 1,285,988 | 11/1918 | Gudebrod | 424/49 |
| 1,336,272 | 4/1920 | Billings | 424/49 |
| 1,411,681 | 4/1922 | Burlew | 424/49 |
| 1,471,987 | 10/1923 | Vogt | 424/49 |
| 1,627,963 | 5/1927 | Fuller | 424/49 |
| 1,633,336 | 6/1927 | Larson | 424/49 |
| 1,716,035 | 6/1929 | Donchi | 424/49 |
| 1,789,052 | 1/1931 | Pfanstiehl | 424/49 |
| 1,839,456 | 1/1932 | Anderson | 424/49 |
| 1,936,456 | 11/1933 | Larson et al. | 424/49 |
| 1,969,874 | 8/1934 | Butterfield | 424/49 |
| 1,989,895 | 2/1935 | Gilder | 424/49 |
| 2,004,957 | 6/1935 | Messner | 424/49 |
| 2,024,146 | 12/1935 | Crowther | 424/49 |
| 2,027,535 | 1/1936 | Jacobson | 424/49 |
| 2,031,233 | 2/1936 | Stillwell | 424/49 |
| 2,035,267 | 3/1936 | Fleischman | 424/49 |
| 2,054,742 | 9/1936 | Elbel | 424/49 |
| 2,069,157 | 1/1937 | Sahyun | 424/49 |
| 2,089,845 | 8/1937 | Atkins | 424/49 |
| 2,124,971 | 7/1938 | Eisenberg et al. | 424/49 |
| 2,154,168 | 4/1939 | Klein et al. | 424/49 |
| 2,224,489 | 12/1940 | Rozenbroek | 424/49 |
| 2,464,755 | 3/1949 | Taub | 424/49 |
| 2,667,443 | 1/1954 | Ashton | 424/49 |
| 2,677,700 | 5/1954 | Jackson et al. | 424/49 |
| 2,748,781 | 6/1956 | Collat | 424/49 |
| 2,778,045 | 1/1957 | Bly et al. | 424/49 |
| 2,896,639 | 7/1959 | Fleming | 424/49 |
| 3,164,524 | 1/1965 | Fand et al. | 424/49 |
| 3,228,845 | 1/1966 | Najjar | 424/49 |
| 3,427,380 | 2/1969 | Kirkland | 424/54 |
| 3,427,381 | 2/1969 | Kirkland | 424/54 |
| 3,431,339 | 4/1969 | Gyarmathy et al. | 424/52 |
| 3,475,533 | 10/1969 | Mayrand | 424/57 |
| 3,574,824 | 4/1971 | Echeandia et al. | 424/50 |
| 3,629,468 | 12/1971 | Anderson | 424/44 |
| 3,639,563 | 2/1972 | Januszewski | 424/49 |
| 3,651,207 | 3/1972 | Lauster et al. | 424/50 |
| 3,729,553 | 4/1973 | Gold et al. | 424/44 |
| 3,772,431 | 11/1973 | Mikvy et al. | 424/44 |
| 3,830,246 | 8/1974 | Gillings | 132/89 |
| 3,864,472 | 2/1975 | Pensak et al. | 424/54 |
| 3,887,701 | 6/1975 | Nachtigal | 424/54 |
| 3,888,976 | 6/1975 | Mikvy et al. | 424/44 |
| 3,907,991 | 9/1975 | Accetta | 424/130 |
| 3,928,618 | 12/1975 | Bauman | 424/58 |
| 3,929,988 | 12/1975 | Barth | 424/54 |
| 3,942,539 | 3/1976 | Corliss et al. | 132/79 |
| 3,943,949 | 3/1976 | Ashton et al. | 132/89 |
| 3,947,570 | 3/1976 | Pensak et al. | 424/54 |
| 3,957,964 | 5/1976 | Grimm, III | 424/10 |
| 3,976,765 | 8/1976 | Nachtigal | 424/54 |
| 4,011,309 | 3/1977 | Lutz | 424/49 |
| 4,029,113 | 6/1977 | Guyton | 132/91 |
| 4,069,312 | 1/1978 | Mannara | 424/49 |
| 4,071,614 | 1/1978 | Grimm, III | 424/49 |
| 4,082,841 | 4/1978 | Pader | 424/50 |
| 4,100,269 | 7/1978 | Pader | 424/49 |
| 4,130,636 | 12/1978 | Tomlinson | 424/52 |
| 4,132,770 | 1/1979 | Barth | 424/39 |
| 4,138,477 | 2/1979 | Gaffar | 424/52 |
| 4,143,126 | 3/1979 | Gaffar | 424/49 |
| 4,150,151 | 4/1979 | Pader et al. | 424/56 |
| 4,152,418 | 5/1979 | Pader | 424/50 |
| 4,158,815 | 6/1979 | Wine | 325/455 |
| 4,170,633 | 10/1979 | Wagenknecht | 424/48 |
| 4,229,017 | 10/1980 | Hagedorn | 280/961 |
| 4,244,307 | 9/1980 | Thiele et al. | 424/49 |
| 4,339,429 | 7/1982 | Raaf et al. | 424/49 |

(List continued on next page.)

FOREIGN PATENT DOCUMENTS

0086440 8/1983 European Pat. Off. .
2128133 4/1984 United Kingdom .

OTHER PUBLICATIONS

J. Afseth et al., Caries Res. 17: 472-475 (1983).

G. Bowden, J. Canad. Dent. Assn., No. 2, 1984, pp. 169-172.

G. Harrap et al., Archs Oral Biol., vol. 29, No. 2, pp. 87-91 (1984).

(List continued on next page.)

Primary Examiner—Ronald W. Griffin
Attorney, Agent, or Firm—Ernest V. Linek

[57] ABSTRACT

This invention relates to a method of treating the oral cavity with ingestible, non-foaming, non aqueous, liquid and semi-solid oral hygiene preparations containing: a nonionic surfactant, a coating substance insoluble in said surfactant and a microbially active form of stannous fluoride.

9 Claims, No Drawings

U.S. PATENT DOCUMENTS

| | | | |
|---|---|---|---|
| 4,343,785 | 8/1982 | Schmolka | 424/49 |
| 4,362,639 | 12/1982 | Eoga | 252/99 |
| 4,370,314 | 1/1983 | Gaffar | 424/54 |
| 4,420,472 | 12/1983 | Boden et al. | 424/58 |
| 4,446,157 | 5/1984 | Boden et al. | 426/3 |
| 4,465,661 | 8/1984 | Schmolka | 424/49 |
| 4,465,663 | 8/1984 | Schmolka | 424/62 |
| 4,476,107 | 10/1984 | Schmolka | 424/49 |
| 4,511,563 | 4/1985 | Schmolka | 514/162 |
| 4,548,219 | 10/1985 | Newman et al. | 132/91 |
| 4,554,154 | 11/1985 | White | 424/16 |
| 4,610,871 | 9/1986 | Lynch | 424/48 |
| 4,657,758 | 4/1987 | Goldemberg et al. | 424/49 |
| 4,774,077 | 9/1988 | Ferlauto et al. | 424/52 |
| 4,840,787 | 6/1989 | Grollier | 424/52 |
| 4,857,303 | 8/1989 | Grollier | 424/52 |
| 4,894,220 | 1/1990 | Nabi et al. | 424/52 |
| 4,902,497 | 2/1990 | Crisanti et al. | 424/49 |
| 4,950,479 | 8/1990 | Hill et al. | 514/901 |

OTHER PUBLICATIONS

G. Harrap et al., Journal of Periodontal Research (1983) 18: 634–642.

R. Havenaar, J. Dent. Res., Feb. 1984, vol. 63, No. 2, pp. 120–123.

A. Jori, Advances in Pharmacology and Chemotherapy, vol. 20, pp. 191–218.

W. Loesche et al., JADA, vol. 106, Apr. 1984, pp. 587–592.

K. Makinen et al., JADA, vol. 111, Nov. 1985, pp. 745–751.

J. Mordenti et al., Journal of Pharmaceutical Sciences, vol. 71, No. 12, Dec. 1982, pp. 1419–1421.

R. Segal et al., Journal of Pharmaceutical Sciences, vol. 74, No. 1, Jan. 1985, pp. 79–81.

Southard et al., JADA, vol. 108, Mar. 1984, pp. 338–341.

Topitsoglou et al., Caries Res. 17:369–378 (1983).

Winter et al., Caries Res. 16:349–352 (1982).

Plaque: Current Approaches to Prevention and Control; JADA, vol. 109, Nov. 1984, pp. 690, 692, 694, 696, 698, 700 & 702.

Fine et al., Journal of Clinical Periodontology, 12: 660–666 (1985).

J. Van Houte, Reviews of Infectious Diseases, vol. 5, Supplement 4, Sep.–Oct. (1983), pp. 5659–5669.

Baker et al.; J. Periodontal Res. 13: 474–485 (1978).

Tanzer et al., Antimicrobial Agents and Chemotherapy, vol. 15, No. 3, 408–414 (1979).

C. Bass, Dent. Items of Interest, 70: 921–934 (1948).

Keene et al., JADA, vol. 93, 328–333 (1976).

Lobene et al., Clinical Preventive Dentistry, vol. 4, No. 1, 5–8 (1982).

Finkelstein et al., J. Dent. Res., vol. 58, No. 3, 1034–1039, (1979).

Wunderlich et al., J. Den. Res., 60, p. 9525, Spec. Iss. A.

Schmid et al., J. Dent. Res., 60, p. 341, Spec. Iss. A.

Wright et al., Clinical Preventive Dentistry, vol. 1, No. 3, (1979), pp. 23–31.

Wright et al., J. Dent. Res., vol. 56, No. 6, (1977), pp. 574–578.

Van Swol et al., Military Medicine, 391–394 (1977).

Horowitz et al., J. Den. Res., 56: 1977 Spec. Iss. A, p. 63.

C. Mayhall, "The Biologic Basis of Dental Caries, Chapter 5, Nonmineralized Coverings of the Enamel Surface", p. 148 only.

METHOD OF TREATING THE ORAL CAVITY WITH ORAL HYGIENE PREPARATIONS CONTAINING ACTIVE $SnF_2$

CROSS-REFERENCE TO RELATED APPLICATIONS

This application is a continuation-in-part of copending application Ser. Nos.: 06/927,752, filed Nov. 6, 1986 and 06/927,805, filed Nov. 6, 1986, now U.S. Pat. No. 4,950,479, the disclosures of which are hereby incorporated herein by reference.

FIELD OF THE INVENTION

This invention relates to a method of treating the oral cavity with ingestible, non-foaming, nonaqueous liquid and semi-solid, oral hygiene preparations containing a nonionic surfactant, a coating substance insoluble in said surfactant, and a microbially active form of stannous fluoride ($SnF_2$) These oral hygiene preparations have utility in treating caries, plaque fighting and in gingivitis control as well as for the treatment of hypersensitive teeth, various Candida so. conditions, and other disorders of the oral cavity. These oral hygiene preparations can be delivered to the oral cavity in several forms including: sprays, pre-rinses, rinses, pastes, gels and creams. Generally the oral hygiene preparations of the present invention are stored and used in dispensers that do not take on oxygen and/or water over the life of the product.

BACKGROUND OF THE INVENTION

Stannous fluoride, $SnF_2$, has been used in dentistry since the 1950's as a chemical adjunct to prevent dental caries. Topical applications of $SnF_2$ consistently have shown dramatic reductions in dental caries activity with minimal side effect. Evidence has also accumulated that $SnF_2$ has antibacterial properties which may affect its anticaries properties as well as inhibit plaque formation and gingivitis. See Tinanoff, "Review of the Antimicrobial Action of Stannous Fluoride," 1990.

Addy et al., 1988, reported a densensitizing effect for fresh $SnF_2$ due to a covering or obturation of tubules in hypersensitive dentine. There is also an indication that $SnF_2$ may be effective in controlling Candida sp. colorization of denture plaque.

Prescription ($R_x$) nonaqueous gels of glycerine and $SnF_2$, such as Scherer Laboratory's, Gel-Kem are perhaps the most widely used form of $R_x$ $SnF_2$ available commercially. These gels are generally prescribed for the treatment of caries, hypersensitive teeth as well as gingivitis.

Unfortunately, in spite of its promising results, the effective use of $SnF_2$ has been drastically limited by its inherent instability in the presence of oxygen, water, abrasives etc.

In addition to the inherent instability of $SnF_2$, most $SnF_2$ products suffer from poor patient compliance, attributed in part to the nonaqueous carriers required to maintain activity, to the metallic taste of the product, as well as to the methods of application, which usually include a brushing step separate and apart from the use of a dentifrice. For example, brush-on $SnF_2$ gels require the patient to brush at least four times/day, i.e., twice with the gel and twice with a regular dentifrice. Compliance in such a treatment regimen drops about 30%, an unacceptable level, as documented by Hastrieter's review of Wolf et al.'s 1989 Gel-Kem study.

With the advent of fluoride in water and fluoridated dentifrices, gum disease, gingivitis, hypersensitive teeth, root caries in the elderly and candida disorders in denture wearers, have replaced caries in children as the dominant oral care concerns of the '90's requiring special treatment. For example, a recent NIH survey established 90% of adults 65 or older have some form of gum disease, and over 123 million adults in the U.S. suffer from gum disease. Moreover, one out of six adults suffer from hypersensitivity at one time or another, while ten million adults are chronic sufferers. Additionally, the millions of adults who undergo periodontal treatment, or have their teeth cleaned, experience hypersensitivity discomfort ranging from an uncomfortable feeling to severe pain. Most denture wearers suffer from "denture breath" attributed in part to Candida sp. colonization of denture plaque and/or plaque-like coatings on dentures.

Recent reviews on dentine hypersensitivity have deduced that the transmission of pain stimuli across dentine is by a hydrodynamic mechanism. This is confirmed by the open tubules (microscopic openings) present at the dentine surface of sensitive teeth (and not present in normal teeth). Various stimuli cause fluid movement in these tubules which activate nerve endings in the pulp.

Considerable evidence has accumulated in the past 20 years to show that topical applications of $SnF_2$ reduce *S. mutans* levels as well as demonstrate antiplaque properties. These antiplaque and antigingivitis benefits of $SnF_2$ appear to be related to frequent, i.e., several times/day treatment with $SnF_2$.

Root caries in the elderly is attributed to the recession of gums and is a common condition in the elderly that fortunately does respond to fluoride treatment. Candida sp. yeast disorders are estimated to occur in approximately 90% of denture wearers. These disorders lead to, or are associated with, stomatitis and thrush (candidiasis).

There is therefore a definite need in the art for oral hygiene preparations containing microbially active $SnF_2$ that retain the desired antibacterial activity over the use life of the preparations. There is also a need in the art for oral hygiene preparations containing microbially active $SnF_2$ that are pleasant to use, encourage compliance and support frequent usage throughout the day. There is a further need in the art for new methods of treating caries, coronal caries, gingivitis, plaque buildup, hypersensitivity and Candida sp. infections of denture plaque with microbially active $SnF_2$ products in various forms.

There is a further need in the art for delivery vehicles for microbially active $SnF_2$ which achieve rapid transport of $SnF_2$ into fissures, crevices in dentures and other prosthesis where the microbial activity of $SnF_2$ can be employed to fight plaque and disrupt the colonization of denture plaque by yeast type organisms while protecting the $SnF_2$ from degradation of its microbial activity.

In view of the foregoing it is an object of this invention to provide an oral hygiene preparation containing a microbially active form of $SnF_2$ for treating caries, gingivitis, plaque buildup hypersensitivity and Candida sp. infections of denture plaque.

It is also an object of this invention to provide an oral hygiene preparation containing microbially active $SnF_2$ that is pleasant to use, encourages compliance and repetitive usage.

It is a further object of this invention to provide an effective method for treating caries, gingivitis, hypersensitivity, plaque buildup and Candida sp. infections of denture plaque.

It is still a further object of this invention to provide a compatible vehicle for microbially active $SnF_2$ that permeates crevices etc. in dentures and denture plaque to deliver the active $SnF_2$ so it can fight denture plaque and control colonization of denture plaque by Candida sp. organisms.

It is yet another object of this invention to provide a method of manufacturing oral hygiene preparations containing a microbially active form of $SnF_2$.

SUMMARY OF THE INVENTION

In accordance with the foregoing objectives, this invention provides oral hygiene preparations containing microbially active forms of stannous fluoride ($SnF_2$) that are useful for treating caries, gingivitis, Candida sp. infections of denture plaque, hypersensitivity and plaque buildup. The preparations of the present invention are ingestible, non-foaming, nonaqueous, abrasive free, liquids and semi-solids that contain a nonionic surfactant, a coating substance insoluble in said surfactant and a microbially active form of $SnF_2$.

The preparations of the present invention can be introduced into the oral cavity in several forms including: sprays, pre-rinses, gels, pastes and creams. Generally, the preparations of the present invention are stored and used in dispensers that are free from oxidation, hydrolysis, and free from any substances that interfere with the microbial activity of $SnF_2$.

The preparations of the present invention are substantive to the hard and soft tissue in the oral cavity and have a pH from between about 3.4 and about 6.5.

DETAILED DESCRIPTION OF THE INVENTION

As described above, the oral hygiene preparations of this invention are ingestible, non-foaming, nonaqueous, abrasive free, liquids and semi-solids that contain a nonionic surfactant, a coating substance insoluble in said surfactant and a microbially active form of $SnF_2$. These preparations are substantive to the hard and soft tissue in the oral cavity.

The term nonaqueous, as used in the present invention, is defined as being essentially free from active water. That is, there is no "active" water available in the preparation to hydrolyze the microbially active $SnF_2$. While some minute amount of water may be present is generally a certainty, under most conditions (e.g., from relative humidity) but such water is not deemed "active" herein.

The term microbially active stannous fluoride, as used in the present invention, is defined as stannous fluoride that exhibits antimicrobial activity towards *S. mutans* when assayed according to either Camosci and Tinanoff, *Journal Dental Research*, 1984, 63: 1121 et. seq., or Ota et al., *Pediatric Dentistry*, March 1989, Vol. II, Number P.21-25.

"Fresh" stannous fluoride exhibits the antimicrobial properties suitable for the purposes of the present invention. However, to avoid any controversy surrounding the use of the term "fresh", i.e., "how-fresh" etc., for the purposes of the present invention this form of stannous fluoride can also be described as being in its "native" solvated state rather than "fresh." Reliance upon chemical assay for $Sn^{++}$ species is not an adequate measurement of $Sn^{++}$ microbial activity, as many stannous ion species are microbially inactive.

The term non-foaming, for the purposes of the present invention, is defined as producing little or no foam during application of the preparation of the invention to the oral cavity, so as to cause no discomfort or gagging.

The term ingestible, as used in the present invention, is defined as capable of being ingested with no risk of danger to the subject being treated.

Free from abrasives, for the purposes of the present invention, is defined as containing no abrasive, nor abrasive-like substance normally used in dentifrices, or containing trace amounts of these substances such that their characteristics abrasive action cannot be perceived nor their adverse effect on microbially active $SnF_2$ established.

Rinse and pre-rinse, for the purposes of the present invention, include those concentrates of rinses and pre-rinses that are to be mixed with water prior to introducing into the oral cavity. Generally these concentrations are dispensed into a cup with 10 to 15 ml of tap water from hermetically sealed package.

The nonionic surfactants, suitable for the present invention include block copolymer mixtures of polyoxyalkylene compounds, i.e., poloxamers including ethylene oxide and propylene oxide poloxamer mixtures; such as those described in U.S. Pat. Nos. 4,343,7B5: 4,465,663; 4,511,563; and 4,476,107, the disclosures of which are hereby incorporated herein by reference. Commercial versions of these nonionic poloxamer surfactants are available from BASF—Wyandotte Co., Wyandotte, MI and include various Pluronics such as Pluronic F108 and F127 and those Pluronics described in "Pluronic & Tetronic Surfactants", BASF Corp., 1987, at page 2. Other suitable nonionic surfactants useful in the gels of the present invention include: polyoxyethylene sorbitan monoleate (Polysorbate 80); polyethylene glycols (Pluracols); nonylphenol ethoxylates (Surfonics); linear alcohol ethoxylates polyethyleneglycol paraisooctypheny/ethers (Tritons's) and those described in Tables I and II below.

The nonionic surfactants in the preparations of the present invention are preferably employed at levels ranging from about 0.1% to about 50% by weight of the composition, and most preferably from about 0.5% to about 10% by weight of the liquid preparations of the invention and up to 30% in the semi-solids. In general, the amount of nonionic surfactant employed can be adjusted to provide the desired degree of cleaning, conditioning, physical form and treatment desired.

In the present invention, a coating substance is employed in combination with the nonionic surfactant component of the preparation. The coating substances suitable for the preparations of the invention are insoluble in the surfactant and can be characterized as follows, they:

1. suppress the tendency of the surfactant to foam,
2. are safely ingestible at the concentrations used,
3. have an affinity for hard and soft surfaces in the oral cavities,
4. are neural, inert and do not support microbiological activity,
5. modify the surface energy properties of gums and teeth such that it is more difficult for food particles, cellular debris and various plaque precursors and formers to attach to these surfaces, 6. form a thin, transparent coating that does not build up on the gums and teeth and is removed by the normal clearing and flushing action of the mouth,
7. impart a pleasant "smooth" feeling to the surfaces of the oral cavity, and
8. retain various flavors and substances on surfaces of the oral cavity imparting an unexpected prolonged flavor effect and do not interfere with the microbial activity of $SnF_2$.

Suitable coating substances for the preparations of the present invention include various silicones insoluble in the nonionic surfactants used in the present invention including polyalkylsiloxanes such as polydimethysiloxanes, such as Dow Corning 360 Medical Fluid at viscosities of 20 to 12,5000 centistokes; Dow Corning Q7-2587 Simethicone Emulsion; Dow Corning 200 Fluids, 60,000 to 100,000 centistokes with the chemical composition $CH_3 SiO[SiO(CH_3)_3]$; all available from Dow Corning, Midland, MI.

The coating substances of the preparations of the present invention are preferably employed at levels ranging from about 0.01 to about 0.5% by weight of the composition; and most preferably from between about 0.05 and about 0.25% by weight of the preparations. For semi-solid preparations of the invention the coating substances are present at from between about 0.05% and about 4% by weight. In general, the amount of coating substance employed is adjusted to provide the desired degree of conditioning and substantivity for the treatment desired.

The weight ratio of nonionic surfactant to coating substance in the preparations of the present invention range from between about 100:1 to about 2:1 and preferably from between about 17:1 to about 3:1.

Stannous fluoride ($SnF_2$) U.S.P. powder, available from Ozark Mahoning, Tulsa, OK, is suitable for the preparations of the present invention. Generally, the stannous fluoride when used in the various preparations of the present invention which are applied directly into the oral cavity is at concentrations from between about 0.05% and about 0.4% by weight.

For those preparations of the present invention which are to be used as dilutable concentrates, such as the pre-rinse and rinse concentrates described below, or as sprays for the treatment of prosthesis; concentrations of $SnF_2$ ranging from between about 0.4% to about 10% by weight can be used. Normally, the upper limit of $SnF_2$ concentration is determined by the solubility of $SnF_2$ in the formulation chosen and safety in use considerations.

The combination of certain nonionic surfactants with certain coating substances and microbially active stannous fluoride in the preparations of the invention, wherein the coating substance is insoluble in the surfactant is novel. The anticaries, antiplaque, gingivitis control relief of hypersensitivity and anti-Candida sp. results obtained with the preparations of the present invention are attributed in part to:

a. the microbial activity of stannous fluoride obtained with these preparations, b. the excellent compliance profile the preparations of the present invention exhibit during clinical evaluations, c. the mouth feel and improved hedonics that characterize these preparations, d. the modes of delivery used to introduce these preparations into the oral cavity, and e. the cleaning, conditioning and treating of hard and soft tissue in the oral cavity that results from the use of the preparations of the invention.

In one embodiment of the present invention, the preparations of the present invention, in liquid form, are delivered to the oral cavity as sprays which include various extenders such as propylene glycol, glycerin, sorbitol/hydrogenated glucose syrup mixtures, and ethanol. These liquid sprays are free from active water and are preferably dispensed into the oral cavity from a hermetically sealed package such as an aerosol spray device. An example of a liquid spray is described in detail in Example 1 below. Illustrative examples of sprays and other liquids of the invention are further described in Table I.

These sprays are particularly useful in reducing plaque and controlling gingivitis, when they are introduced into the oral cavity several times per day, thereby capitalizing on the substantivity of the microbially active stannous fluoride. When used four to five times per day these sprays have the potential to maintain microbially active stannous fluoride in the oral cavity at levels sufficient to control plaque buildup, reduce bleeding sites and gingivitis and treat Candida sp. infections.

The sprays of the present invention can also be used to treat hypersensitive teeth and root caries in the elderly as well as caries in youngsters. The sprays described herein have the highest compliance potential of all the delivery forms of the preparations of the present invention, not only because of their advanced hedonics but also due to their convenient form of delivery, i.e., the sprays can be carried in pocket or purse and can be used anywhere throughout the day.

The sprays can also be applied to prosthesis to clean, condition and treat the prosthesis for Candida sp. contamination which leads to stomatitis and thrush. See Table I.

In a second embodiment of the invention the preparations of the present invention, in a liquid form, are delivered to the oral cavity as rinses or pre-rinses which include various extenders, etc. such as described in detail in the examples below. These concentrated rinses and pre-rinses are preferably dispensed from a hermetically sealed dispenser or a collapsible tube into a container and diluted with water prior to use. Illustrative Examples of the rinse, pre-rinse concentrates of the present invention are described in Table II below.

The rinse and pre-rinse concentrates of the present invention are particularly useful in fighting plaque, reducing plaque buildup and controlling gingivitis. The rinses and pre-rinse concentrate modes of delivery can also be used as anticaries and hypersensitivity treatments and in this regard are particularly useful for treating root caries and hypersensitive teeth in the elderly.

In another embodiment of the invention, the preparations of the present invention, in a semi-solid form such as a paste, are delivered to the oral cavity from various sealed dispensers including collapsible tubes. Preferably, these pastes are brushed onto the surfaces of the teeth and gums or rubbed into these surfaces with a finger or a swab or a gauze. Illustrative examples of the pastes of the present invention are described below.

The pastes of the present invention are particularly useful in treating root caries and hypersensitive teeth in adults. These pastes are generally applied to the areas to be treated by dispensing the paste onto a finger and rubbing the finger over the area to be treated. When the pastes are dispensed from collapsible tubes ranging from about ⅛ oz. to about 1 oz. in size, they can be carried in pocket or purse and easily applied several items a day outside the bathroom. Generally, the patient also brushes their teeth twice a day with a traditional dentifrice applying the paste after each brushing. Regular use of a traditional dentifrice generally controls the staining that can occur with certain patients who use microbially active stannous fluoride.

In still another embodiment of the invention the preparations of the present invention, in a gel form, are delivered to the oral cavity from various sealed dispensers, including collapsible tubes. Preferably these gels are brushed onto the surfaces of the teeth and gums or rubbed onto these surfaces with a finger or gauze or a swab. Illustrative examples of the gels of the present invention are described in Table II below.

The gels of the present invention are particularly useful in treating gum disease, gingivitis and plaque buildup. They can be dispensed from convenient size tubes that can be carried in pocket or purse and applied throughout the day to the area to be treated. Generally, they are applied after brushing with a traditional dentifrice. It is not necessary to rinse the gels from the mouth since they are pleasant tasting. These gels are perceived to be present and working often times 30 minutes after they have been applied to the area to be treated.

In yet another embodiment of the invention the preparations of the present invention, in a cream form, are delivered to the oral cavity from various sealed dispensers including collapsible tubes. Preferably, these creams are brushed or rubbed onto the surfaces to be treated using a soft bristled brush, a finger or a swab. Illustrative examples of these creams are described in Table III below.

The creams of the present invention are particularly useful in treating gum disease, gingivitis and plaque buildup. They can be dispensed from convenient size tubes that can be carried in pocket or purse and applied throughout the day to the areas to be treated. Generally they are applied after brushing with a dentifrice. It is not necessary to rinse after applying these creams, since they are most pleasant tasting and leave a fresh clean feeling in the mouth.

The cleaning of plaque-like films from the teeth and gums with the preparations of the present invention is achieved with a minimum of mechanical action and without foaming. After the cleaning and treating step there is no need to expectorate nor to rinse the preparation of the present invention from the mouth. The coating that remains on the surfaces of the oral cavity leaves these surfaces feeling smooth and clean. This coating contains an appropriate flavorant, such that the continuing treatment is a pleasant experience which encourages compliance, i.e., regular usage.

The films remaining on the surfaces of the oral cavity are not metabolizable by resident oral cavity microorganisms and are substantive to various surfaces of the oral cavity, unlike natural film formers such as lecithin which are also substantive to soft tissue, but which are metabolizable and support biological activity. See for example, Menaker, *The Biologic Basis of Dental Caries,* Chapter 16, Gibbon and Hoote, *Ann. Rev. of Microbiology,* 29: 19–44; and Hayes, *J. Dent. Res.,* 2: 2–5.

The coating that remains on the hard and soft surfaces of the oral cavity after applying the preparations of the present invention is inert and substantive to the surfaces in the oral cavity. As long as this film remains on these surfaces it:

1. disrupts the subsequent formation of "plaque-like" films on the gums,
2. imparts a smooth feeling,
3. prolongs the pleasant perception of the flavorants used in the preparation. This prolonged flavor perception is particularly novel and unexpected and is a critical contributing factor in the high compliance profile of the preparation of the present invention, and
4. treats the condition in the mouth with microbially active stannous fluoride.

High compliance potential is a critical element of the preparations of the present invention. That is, the pleasant mouth feel and low foaming properties of these preparations and the prolonged pleasant taste and mouth feel that remains after using the preparations of the present invention encourages their regular use. There is a "it's working" perception of the preparations of the invention without negative medicinal connotations which tend to reduce usage and lower compliance potential.

Additional adjuvants can be included in the preparations of the present invention including:

a. Anhydrous carbohydrate sweeteners such as sorbitol and Lycasin, and hydrogenated glucose syrup, in concentrations ranging between about 1 and about 15% by weight.

b. Artificial sweeteners such as acid saccharin in concentrations from between about 0.05 and about 3.0% by weight.

c. Anhydrous humectants such as glycerine and propylene glycol and mixtures thereof at concentrations from between about 5 and about 50% by weight.

d. flavors such as IFF vanillin 101, spearmint 082 in concentrations from between about 0.1 and about 2% by weight, e. anhydrous viscosofiers solids such as hydroxypropylcellulose, methylcellulose and carboxymethylcellulose, and f. miscellaneous additives such as triacetin, 1–3 butylene glycol, benzyl benzoate, A-46 hydrocarbon propellant, isopentane propellant, isobutane propellant in concentrations such as set out in Table I below.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLE 1

A spray containing one of the liquid preparations of the present invention was prepared containing the following substances at the % by weight indicated in parenthesis:

Sorbitol (7.5), glycerin (25) propylene glycol (23.2), absolute ethanol (40), flavor (1), saccharin (0.4), Pluronic L-64 (1.5), silicone 200 (0.04), Lycasin 85% (1), and 40 mesh stannous fluoride (0.4).

This spray preparation was prepared as follows: a glass beaker containing sorbitol, glycerin and Lycasin was magnetically stirred and heated under nitrogen to 120° C.±10°. Stannous fluoride was added with stirring until no solids remained. In a small beaker at 120° C., Pluronic L-64 was added and stirred while Silicone 200 was added to effect a hot-melt emulsion. This emulsion was added over one minute to the solution of stannous fluoride with rapid stirring. Another beaker was stirred at ambient temperature while anhydrous ethanol, propylene glycol, saccharin and flavor was added with stirring. The stannous fluoride was added slowly with stirring and shortly after the addition was complete, the solution became clear. The contents were then maintained under nitrogen.

The stannous fluoride solution was packaged in various dispensers ranging from pumps to aerosols and was suitable for use in treating conditions ranging from gingivitis, caries, Candida infections, to sensitive teeth as well as for cleaning and treating various prosthesis for the control of Candida contamination.

Additional Examples 2-15, of liquid preparations of the invention are illustrated in Table I below.

TABLE I
EXAMPLES OF LIQUID COMPOSITIONS

| EXAMPLE | SURFACTANT | % | COATING SUBSTANCE | % | ABSOLUTE ETHANOL % |
|---|---|---|---|---|---|
| 2 | Pluronic F127 | 0.2 | Dow Corning 200 cs 350 | 0.02 | 38.18 |
| 3 | Pluronic L64 | 0.5 | Dow Corning 200 cs 350 | 0.05 | 37.85 |
| 4 | Pluronic L64 | 1.0 | Dow Corning 200 cs 350 | 0.1 | 37.10 |
| 5 | Pluronic L64 | 2.0 | Dow Corning 200 cs 350 | 0.2 | 35.4 |
| 6 | Pluronic L64 | 4.0 | Dow Corning 200 cs 350 | 0.4 | 33.8 |
| 7 | Pluronic L64 | 2.0 | Dow Corning 200 cs 100 | 0.2 | 36.0 |
| 8 | Pluronic L64 | 2.0 | Dow Corning 200 cs 1000 | 0.2 | 36.0 |
| 9 | Pluronic L64 | 2.0 | Dow Corning 360 cs 12,500 | 0.2 | 36.0 |
| 10 | Pluronic L64 | 1.0 | Dow Corning 1,500 | 0.1 | 48.0 |
| 11 | PEG 400 | 2.0 | Dow Corning 360 cs 350 | 0.1 | 55.7 |
| 12 | T-MAZ-20 | 2.0 | Dow Corning 200 cs 350 | 0.2 | 51.2 |
| 13 | Pluronic L64 | 0.5 | Dow Corning 360 cs 100 | 0.1 | — |
|  | Pluronic L81 | 0.5 | Dow Corning 360 cs 12,500 | 0.1 |  |
|  | Pluronic P85 | 0.5 |  |  |  |
| 14 | Pluronic P85 | 3.0 | Dow Corning 200 cs 100 | 0.4 | 41.7 |
|  | ethoxylated linear C18–C20 alcohols | 1.0 |  |  |  |
| 15 | Pluronic P85 | 1.0 | Dow Corning 1500 | 0.1 | 37.0 |
|  | PEG 400 | 0.5 |  |  |  |
|  | ethoxylated sorbitan laurate | 1.0 |  |  |  |

| EXAMPLE | ANHYDROUS GLYCERIN % | ANHYDROUS PROPYLENE GLYCOL % | ANHYDROUS CARBOHYDRATE SWEETENER | % |
|---|---|---|---|---|
| 2 | 25 | 25 | Sorbitol/Lycasin | 7.5/2.5 |
| 3 | 25 | 25 | Sorbitol/Lycasin | 7.5/2.5 |
| 4 | 25 | 25 | Sorbitol/Lycasin | 7.5/2.5 |
| 5 | 25 | 25 | Sorbitol/Lycasin | 7.5/2.5 |
| 6 | 21.4 | 20 | Sorbitol/Lycasin | 10.0/5.0 |
| 7 | 25 | 25 | Sorbitol/Lycasin | 10.0/5.0 |
| 8 | 25 | 25 | Sorbitol/Lycasin | 10.0/5.0 |
| 9 | 25 | 25 | Sorbitol/Lycasin | 10.0/5.0 |
| 10 | 20 | 15 | Sorbitol | 8.0 |
| 11 | 15 | 10 | Lycasin | 5.0 |
| 12 | — | 20 | — | — |
| 13 | 20 | 20 | Sorbitol/Lycasin | 7.5/2.5 |
| 14 | 30 | — | Sorbitol/Lycasin | 4.0/1.0 |
| 15 | 20 | 20 | — | — |

| EXAMPLE | ACID SACCHARIN % | FLAVOR | % | MISCELLANEOUS | % |
|---|---|---|---|---|---|
| 2 | 0.4 | IDD 101 | 1.0 | — | — |
| 3 | 0.4 | IFF 101 | 1.0 | — | — |
| 4 | 0.4 | IFF 101 | 1.0 | — | — |
| 5 | 0.4 | IFF 101 | 1.0 | — | — |
| 6 | 0.8 | IFF 101 | 1.0 | — | — |
| 7 | 0.8 | IFF 101 | 1.0 | — | — |
| 8 | 0.8 | IFF 101 | 1.0 | — | — |
| 9 | 0.8 | IFF 101 | 1.0 | — | — |
| 10 | 0.5 | IFF 082 | 2.0 | Triacetin | 5 |
| 11 | 0.8 | IFF 082 | 1.0 | 1-3 butylene glycol | 10 |
| 12 | 1.2 | IFF 101 | 5.0 | Benzyl benzoate | 5 |
|  |  |  |  | A-46-hydrocarbon propellant | 15 |
| 13 | 0.4 | IFF 082 | 1.0 | Isopentane propellant | 16 |
| 14 | 1.5 | IFF 082 | 3.0 | Isobutane propellant | 10 |
| 15 | 2.0 | IFF 101 | 3.0 | A-46-hydrocarbon propellant | 15 |

| EXAMPLE | $SnF_2$ Powder % | SPECIFIC TREATMENT |
|---|---|---|
| 2 | 0.2 | Oral cavity anticaries treatment |
| 3 | 0.2 | Oral cavity antiplaque treatment |
| 4 | 0.4 | Oral cavity for gingivitis treatment |
| 5 | 2.0 | Rinse concentrate for hypersensitive teeth |
| 6 | 4.0 | Rinse concentrate for denture treatment |
| 7 | 0.4 | Oral cavity hypersensitive teeth treatment |

TABLE I-continued

| EXAMPLES OF LIQUID COMPOSITIONS | | |
|---|---|---|
| 8 | 0.4 | Oral cavity gingivitis treatment |
| 9 | 0.4 | Oral cavity anticaries treatment |
| 10 | 0.4 | Oral cavity antiplaque treatment |
| 11 | 0.4 | Oral cavity gingivitis treatment |
| 12 | 0.4 | Denture treatment spray |
|  | 0.4 |  |
| 13 | 8.0 | Rinse concentrate spray for gingivitis, anticaries, plaque fighting and hypersensitive teeth treatment |
| 14 | 4.0 | Rinse concentrate spray for treating denture |
| 15 | 0.4 | Denture treatment spray |

All of the above described examples (Table I) can be modified with various nonionic viscosofiers to affect mouth feel, physical appearance and the rate at which the dissolved propellant hydrocarbons effervesce from a pressurized spray. For example, methylcellulose, hydroxypropyl methyl cellulose and hydroxypropyl cellulose, singly or in combinations at concentrations from 0.1% to 2% are particularly efficacious.

Examples 16-22 illustrative of semi-solid preparations of the invention are described in Table II below.

TABLE II

| | | | SEMI-SOLIDS | | | | | |
|---|---|---|---|---|---|---|---|---|
| EXAMPLE | SURFACTANT | % | COATING SUBSTANCE | % | GLYCERINE % | | FLAVOR | % |
| 16 | Pluronic F127 | 30 | Dow Corning 1500 | 6.3 | 20 | | IFF 101 | 0.3 |
| 17 | Pluronic F127 | 12 | Dow Corning 360 | 2.0 | 15 | | IFF 082 | 0.6 |
|  | Pluronic L64 | 10 | Medical cs 12,500 | | | | | |
|  | Pluronic P85 | 10 | | | | | | |
| 18 | Pluronic F127 | 20 | Dow Corning 200 cs 100 | 10 | 11 | | IFF 101 | 0.5 |
| 19 | Pluronic P85 | 25 | Dow Corning 200 | 5 | 10 | | IFF 101 | 0.2 |
|  | Pluronic L64 | 25 | cs, 65,000 | | | | IFF 082 | 0.1 |
| 20 | Pluronic P85 | 15 | Dow Corning 1500 | 10 | 5 | | IFF 101 | 0.4 |
|  | ethoxylated sorbitan laurate | 5 | | | | | IFF 082 | 0.1 |
| 21 | Pluronic F127 | 20 | Dow Corning 200 | .5 | 11.5 | | IFF 101 | 0.2 |
|  | polyethylene glycol 400 | 4 | cs. 350 | | | | | |
| 22 | Pluronic F127 | 20 | Dow Corning 200 | 1.1 | 15.0 | | IFF 082 | 0.5 |
|  | polyethylene glycol 400 T-MAZ-20 | 10 | cs. 10,000 | | | | | |

| EXAMPLE | SOLIDS | % | ABSOLUTE ETHANOL % | ANHYDROUS CARBOHYDRATE SWEETENER | % | ACID SACCHARIN % |
|---|---|---|---|---|---|---|
| 16 | hydroxypropyl cellulose | 2.6 | 20 | Sorbitol | 15 | .4 |
|  |  |  |  | Lycasin | 5 |  |
| 17 | hydroxypropyl cellulose | 3 | 10 | 14.6 Sorbitol | 10 | .4 |
|  | methyl cellulose | 2 |  | Lycasin | 10 |  |
| 18 | hydroxypropyl cellulose | 3 | — | 10.0 Sorbitol | 20 | .2 |
|  | carboxymethyl cellulose | 5 |  | Lycasin | 20 |  |
| 19 | — | — | 10 | 10 Lycasin | 13 | .4 |
| 20 | carboxymethyl cellulose | 10 | 5 | 12 Sorbitol | 30 | — |
|  | hydroxypropyl cellulose | 2.3 |  | Lycasin | 5 |  |
| 21 | hydroxypropyl methyl cellulose | 3 | 20 | Sorbitol | 10 | .4 |
|  |  |  |  | Lycasin | 10 |  |
| 22 | hydroxypropyl methyl cellulose (fines) | 10 | — | — Sorbitol (fine powder) | 33 | — |

| EXAMPLE | SnF$_2$ POWDER % | FORM OF PREPARATION | SPECIFIC TREATMENT |
|---|---|---|---|
| 16 | 0.4 | cream gel | denture treatment |
| 17 | 0.4 | gel | hypersensitive teeth treatment |
| 18 | 0.3 | paste | anticaries and antigingivitis treatment |
| 19 | 1.3 | cream | denture treatment, to be used with regular toothpaste |
| 20 | 0.2 | paste | hypersensitive teeth treatment |
| 21 | 0.4 | gel | denture wearers, oral cavity anti-thrush treatment |
| 22 | 0.4 | paste | AIDS patient, oral cavity treatment; and stomatitis treatment |

The basic method of manufacturing the preparations of the present invention has been described in Example 1. Generally, SnF$_2$ is sufficiently soluble in the polyhydric adjuvants used in the preparations of the present invention such as glycerine, propylene glycol and sorbitol to allow formulating the concentration of Sn$_2$ desired. The requisite SnF$_2$ powder is dissolved in heated mixtures of these polyhydric adjuvants present in the preparations of the invention such as described in Table I and II above.

A melt-emulsion of the otherwise incompatible components of the preparations of the present invention, including the surfactant, coating substance and flavor oil is formed as described in Example 1, and this emulsion is blended with the polyhydric/SnF$_2$ solution.

When viscosofiers are required, they are preferably suspended in a component such as glycerine and this suspension is then added to the remainder of the preparation of the invention with vigorous agitation.

To assure SnF$_2$ stability during manufacturing of the preparations of the present invention, water and air are excluded during the various processing steps.

Specifically, those components that typically contain traces of water, i.e., the polyhydric components can be placed in a jacketed, vacuum pressure vessel and heated until the water has been distilled off. The vessel can then be blanketed with an inert gas such as nitrogen prior to the introduction of SnF$_2$.

Subsequent mixing and packaging steps are carried out under similar water and oxygen restricted conditions. Packaging materials are generally selected on basis of their water and oxygen barrier properties.

Particularly preferred packages suitable for the preparations of the present invention include hermetically sealed dispensers such as aerosols, collapsible tubes, pressure assist pump dispensers, single dose sealed packages and barrier aerosol dispensers such as the Sepro ® dispenser.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The method of treating the oral cavity with an oral hygiene preparation, comprising a nonionic surfactant, a coating substance insoluble in said surfactant and SnF$_2$;
   wherein said preparation:
   a. is non-aqueous, abrasive free, and free from substance that interfere with the microbial activity of SnF$_2$,
   b. is characterized as ingestible, non-foaming, and substantive to hard and soft tissue in the oral cavity,
   c. has a pH from between about 3.4 and about 6.5, and
   d. is antimicrobially active towards *s. mutans*,
   said method comprising the steps of periodically introducing said preparation into the oral cavity in one of several forms selected from the group consisting of sprays, rinses, pastes, gels and creams and retaining said preparation therein for a period of time sufficient to treat or prevent caries, plaque and/or gingivitis therein;
   said preparation being conveniently stored in and dispensed from a container that is free from water and oxygen over the useful life of the preparation.

2. A method of treating the oral cavity for caries with a liquid, oral hygiene preparation, comprising a nonionic surfactant, a coating substance insoluble in said surfactant and SnF$_2$;
   wherein said preparation:
   a. is nonaqueous, abrasive free, and free from substances that interfere with the microbial activity of SnF$_2$,
   b. is characterized as ingestible, non-foaming, and substantive to hard and soft tissue in the oral cavity,
   c. has a pH from between about 3.4 and about 6.5, and
   d. is antimicrobially active towards *S. mutans*, and wherein said preparation is periodically introduced into the oral cavity as a spray dispensed from a hermetically sealed dispenser.

3. A method of treating the oral cavity to reduce plaque buildup and control gingivitis with a liquid oral hygiene preparation, comprising a nonionic surfactant, a coating substance insoluble in said surfactant and SnF$_2$;
   wherein said preparation:
   a. is nonaqueous, abrasive free, and free from substances that interfere with the microbial activity of SnF$_2$,
   b. is characterized as ingestible, non-foaming, and substantive to hard and soft tissue in the oral cavity,
   c. has a pH from between about 3.4 and about 6.5, and
   d. is antimicrobially active towards *S. mutans*. and wherein said preparation is periodically introduced into the oral cavity as a spray dispensed from a hermetically sealed dispenser.

4. A method of treating the oral cavity to fight caries and reduce hypersensitivity with a semi-solid, oral hygiene preparation, comprising a nonionic surfactant, a coating substance insoluble in said surfactant and SnF$_2$;
   wherein said preparation:
   a. is nonaqueous, abrasive free, and free from substances that interfere with the microbial activity of SnF$_2$,
   b. is characterized as ingestible, non-foaming, and substantive to hard and soft tissue in the oral cavity,
   c. has a pH from between about 3.4 and about 6.5, and
   d. is antimicrobially active towards *S. mutans*, and wherein said preparation is periodically introduced into the oral cavity as a paste, dispensed from a collapsible tube.

5. A method of treating the oral cavity to reduce plaque buildup and control gingivitis with a liquid concentrate, oral hygiene preparation, comprising a nonionic surfactant, a coating substance insoluble in said surfactant and SnF$_2$;
   wherein said preparation:
   a. is nonaqueous, abrasive free, and free from substances that interfere with the microbial activity of SnF$_2$,
   b. is characterized as ingestible, non-foaming, and substantive to hard and soft tissue in the oral cavity,
   c. has a pH from between about 3.4 and about 6.5, and
   d. is antimicrobially active towards *S. mutans*. and wherein said preparation is periodically introduced into the oral cavity as a rinse or pre-rinse concentrate that is diluted with water after being dispensed from a hermetically sealed dispenser.

6. A method of treating the oral cavity to control *S. mutans* activity with semi-solid, oral hygiene preparation, comprising a nonionic surfactant, a coating substance insoluble in said surfactant and $SnF_2$;

wherein said preparation:
a. is nonaqueous, abrasive free, and free from substances that interfere with the microbial activity of $SnF_2$,
b. is characterized as ingestible, non-foaming, and substantive to hard and soft tissue in the oral cavity,
c. has a pH from between about 3.4 and about 6.5, and
d. is antimicrobially active towards *S. mutans*. and wherein said preparation is periodically introduced into the oral cavity as a gel, dispensed from a collapsible tube.

7. A method of treating the oral cavity to control *S. mutans* activity with semi-solid, oral hygiene preparation, comprising a nonionic surfactant, a coating substance insoluble in said surfactant and $SnF_2$;

wherein said preparation:
a. is nonaqueous, abrasive free, and free from substances that interfere with the microbial activity of $SnF_2$,
b. is characterized as ingestible, non-foaming, and substantive to hard and soft tissue in the oral cavity,
c. has a pH from between about 3.4 and about 6.5, and
d. is antimicrobially active towards *S. mutans,* and wherein said preparation is periodically introduced into the oral cavity as a cream, dispensed from a collapsible tube.

8. A method of treating prosthesis, to control plaque buildup and candida species contamination with a spray oral-hygiene preparation, comprising a nonionic surfactant, and $SnF_2$;

wherein said preparation:
a. is nonaqueous, abrasive free, and free from substances that interfere with the microbial activity of $SnF_2$,
b. is characterized as ingestible, non-foaming, and substantive to hard and soft tissue in the oral cavity,
c. has a pH from between about 3.4 and about 6.5, and
d. is antimicrobially active towards *S. mutans,* and wherein said preparation is periodically sprayed onto the prosthesis, from an aerosol spray.

9. A method of treating prosthesis, to control plaque buildup and candida species contamination with a rinse concentrate oral-hygiene preparation, comprising a nonionic surfactant, a coating substance insoluble in said surfactant and $SnF_2$;

wherein said preparation:
a. is nonaqueous, abrasive free, and free from substances that interfere with the microbial activity of $SnF_2$,
b. is characterized as ingestible, non-foaming, and substantive to hard and soft tissue in the oral cavity,
c. has a pH from between about 3.4 and about 6.5, and
d. is antimicrobially active towards *S. mutans,* and wherein said preparation is periodically diluted and the prosthesis to be treated are soaked in said rinse.

* * * * *